United States Patent [19]

Keilhauer et al.

[11] Patent Number: 5,789,418

[45] Date of Patent: Aug. 4, 1998

[54] BIS-NAPHTHALIMIDES FOR THE TREATMENT OF CANCER

[75] Inventors: Gerhard Keilhauer, Dannstadt-Schauernheim, Germany; Cynthia Romerdahl, Wayland, Mass.; Miguel Fernandez Braña, Madrid, Spain; Xiao-Dong Qian, Wellesley; Peter Bousquet, Leominster, both of Mass.; José Maria Castellano Berlanga, Madrid, Spain; Marina Moran Moset, Madrid, Spain; Maria Jesus Perez De Vega, Madrid, Spain

[73] Assignee: BASF Aktiengesellschaft, Ludwigshafen, Germany

[21] Appl. No.: 802,013

[22] Filed: Feb. 18, 1997

Related U.S. Application Data

[60] Division of Ser. No. 287,421, Aug. 9, 1994, Pat. No. 5,616,589, which is a continuation-in-part of Ser. No. 108,949, Aug. 18, 1993, abandoned.

[51] Int. Cl.$^6$ .................. C07D 221/14; C07D 401/12; C07D 221/18; A61K 31/445
[52] U.S. Cl. .................................................. 514/296
[58] Field of Search ........................... 514/284, 296

[56] References Cited

U.S. PATENT DOCUMENTS

| | | | |
|---|---|---|---|
| 4,874,863 | 10/1989 | Braña et al. | 540/99 |
| 5,086,052 | 2/1992 | Ardecky | 514/284 |
| 5,086,059 | 2/1992 | Ardecky et al. | 514/284 |
| 5,554,622 | 9/1996 | Braña et al. | 514/284 |

FOREIGN PATENT DOCUMENTS

| | | |
|---|---|---|
| 0506008 A1 | 9/1993 | European Pat. Off. . |
| 3535496 A1 | 4/1987 | Germany . |
| WO 93/12092 | 6/1993 | WIPO . |

OTHER PUBLICATIONS

Peckham et al, Ed, "Oxford Textbook of Oncology, vol. 1", pp. 445–453 (1995).

Bousquet, Peter F. et al., "Preclinical Evaluation of LU 79553: A Novel Bis–naphthalimide with Potent Antitumor Activity," *Cancer Research* 55:1176–1180 (1995).

*Primary Examiner*—Mark L. Berch
*Attorney, Agent, or Firm*—Hamilton, Brook, Smith & Reynolds, P.C.

[57] ABSTRACT

Disclosed herein are compounds pharmaceutical compositions containing same of the formula
1. A compound of the Formula

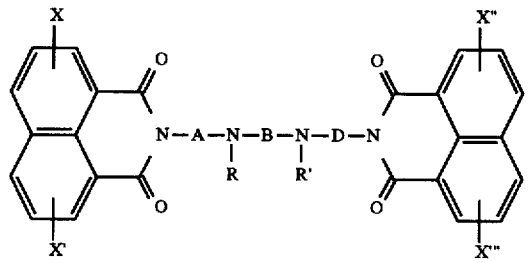

wherein X, X', X" and X'", A, B, D, R, and R' are as identified in the specification and their preparation. Pharmaceutical compositions containing same can be used in the treatment of cancer.

7 Claims, No Drawings

BIS-NAPHTHALIMIDES FOR THE TREATMENT OF CANCER

RELATED APPLICATIONS

This application is a divisional of U.S. application Ser. No. 08/287,421 filed Aug. 9, 1994, now U.S. Pat. No. 5,616,589 which is a continuation-in-part of U.S. application Ser. No. 08/108,949, filed Aug. 18, 1993 now abondoned. All of the above applications are incorporated herein by reference in their entirety.

FIELD OF THE INVENTION

This invention relates to new bis-naphthalimides and their salts, processes for their preparation, pharmaceutical compositions containing them and methods of using them to treat malignancies in a mammal, particularly solid tumor carcinomas such as colon carcinoma, breast tumors, prostate cancer and non-small lung carcinoma.

BACKGROUND OF THE INVENTION

Harnish et al., U.S. Pat. No. 4,841,052 issued Jun. 20, 1989 discloses bis-naphthalic acid imides useful as charge-regulating substances in electrophotographic toners.

Braña et al., U.S. Pat. No. 4,874,883 issued Oct. 17, 1989 discloses anticancer compounds of the formula:

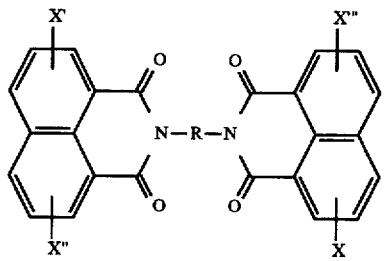

wherein X, X', X" and X'" are identical or different and are each H, $NO_2$, $NH_2$, $C_1$–$C_6$ alkylamino, di-$C_1$–$C_6$ alkylamino, OH, $C_1$–$C_6$ alkoxy, halogen, trihalomethyl, $C_1$–$C_6$ alkyl, formyl, $C_1$–$C_6$ alkylcarbonyl, ureyl,$C_1$–$C_6$ alkylureyl and R is a straight chain or branched $C_4$–$C_{10}$ alkylene which is interrupted at one or two points in the chain by a secondary or tertiary amino group, where 2 nitrogen atoms may additionally be bonded to one another by an alkylene group, or a salt with a physiologically tolerated acid.

Ardecky et al., U.S. Pat. No. 5,086,059, issued Feb. 4, 1992 discloses naphthalimides containing an ethano bridge across the 4 and 5 positions of the naphthalimide ring. Those compounds were said to be efficacious against cancer and more soluble in aqueous media than prior art compounds.

Sun, U.S. Pat. No. 5,206,249, issued Apr. 27, 1993, discloses bisnaphthalimides with naphthalimide rings containing at least one nitro substituent, joined by branched bridging moieties as anticancer drugs. Sun et al, PCT/US92/10525, published 24 Jun. 1993 discloses bis-naphthalimides with naphthalimide rings containing at least one nitro substituent, joined by branched bridging moieties.

Braña et al. 1992 Germ. Pat. Appln. 42 32 739.3 Sep. 30, 1992, discloses asymmetric bis-naphthalimides.

Harnish, U.S. Pat. No. 4,919,848, discloses bisnaphthalimides which are intermediates for the preparation of compounds for quenching the fluorescence generated by anionic optical brighteners.

Heretofore it had been thought that substitution, particularly nitro substitution, on the naphthalimide ring(s) is important for anti-tumor efficacy of bis-naphthalimides, whether via interactions involved in DNA intercalation of the nitrobisnapthalimide or otherwise. We have surprisingly found, however, that such nitro substitution is not required for anti-tumor activity after all, and in fact, that certain bisnaphthalimides which lack nitro substitution and/or which have new combinations of ring substituents and bridge geometry, as described in detail below, provide anti-tumor compositions with improved toxicity profiles, anti-tumor selectivity and/or solubility.

DESCRIPTION OF THE INVENTION

This invention relates to bis-naphthalimide compounds of Formula I (including the individual enantiomeric or diasteriomeric forms thereof, mixtures of such enantiomeric or diasteriomeric forms and the pharmaceutically acceptable acid addition salts thereof), pharmaceutical compositions containing these compounds and methods of using them for treating cancer in a mammal:

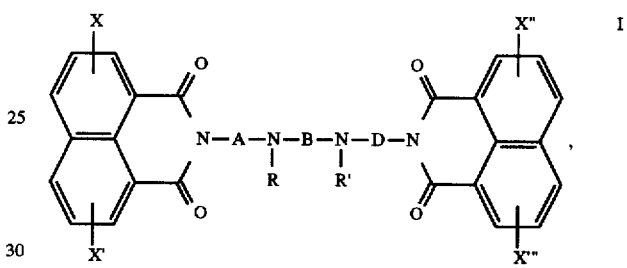

wherein X, X', X" and X'" are identical or different and are selected from the group consisting of H, $NO_2$, $NH_2$, NH-lower acyl, $C_{1-6}$ alkylamino, di-$C_{1-6}$ alkylamino, OH, $C_{1-6}$ alkoxy, halogen, trihalomethyl, $C_{1-6}$ alkyl, formyl, $C_{1-6}$ alkylcarbonyl, ureyl, and $C_{1-6}$ alkylureyl or X and X' or X" and '" may form an ethylene bridge between C-4 and C-5 on the ring system. R and R' are H, $C_{1-4}$ alkyl, aryl or benzyl; A is—$CH_2$—$CH_2$—, which may be optionally substituted with a $C_{1-4}$ alkyl substituent; and replaced by $CC_{1-4}$-alkyl group-B is—$(CH_2)_n$—, wherein n is 3 or 4, and wherein one hydrogen atom may be replaced by a $C_{1-4}$-alkyl group.

One class of compounds of this invention are bis-naphthalimides of Formula I in which at least one of X, X', X" and X'" are not H, i.e., wherein X, X', X" and X'" are identical or different and are selected from the group consisting of $NO_2$, $NH_2$, NH-lower acyl, $C_{1-6}$ alkylamino, di-$C_{1-6}$ alkylamino, OH, $C_{1-6}$ alkoxy, halogen, trihalomethyl, $C_{1-6}$ alkyl, formyl, $C_{1-6}$ alkylcarbonyl, ureyl, and $C_{1-6}$ alkylureyl. It is currently preferred in various embodiments of this class that none of X, X', X" and X'" are $NO_2$.

One sublass of the foregoing are bis-naphthalimides of Formula I wherein at least one of X, X', X" and X'" is $NH_2$, NH-lower acyl, $C_1$–$C_6$ alkylamino or di-$C_1$–$C_6$ alkylamino. This class includes among others, compounds of Formula I in which X and X" are H and X' and X' are $NHCOCH_3$.

Another class of such compounds are bis-naphthalimides of Formula I wherein the bridging moiety joining the two ring systems is:

wherein R is as previously defined. These compounds include those in which X, X', X" and X'" and R are all H a compound which is preferred.

Symmetric compounds of this invention can be synthesized by reacting a naphthalic anhydride of Formula II with a half equivalent of a polyamine of Formula III, in an organic solvent such as, dioxane, ethanol, DMF, etc. at a temperature ranging from –20° C. to the solvent boiling temperature (Scheme 1). The solid is filtered from the reaction mixture, or the reaction mixture is evaporated to dryness under reduced pressure and the residue purified by conventional means such as crystallization or chromatography.

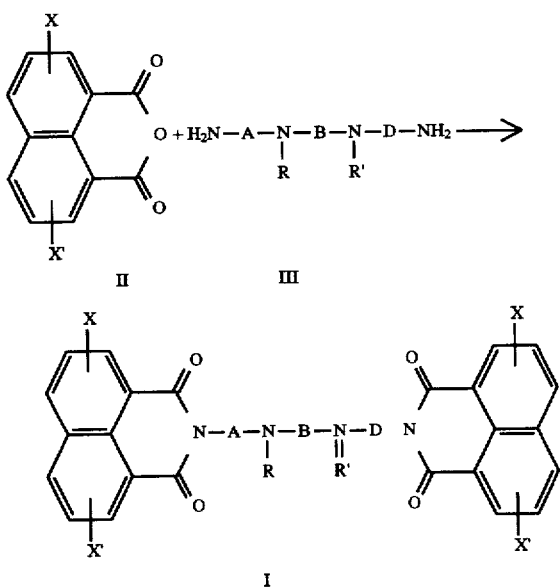

Scheme 1

Asymmetric compounds can be synthesized by conventional protection of one of the amino termini of the polyamine (III) until condensation thereof with an equivalent of anhydride. Condensation of the resulting product with another equivalent of anhydride is then conducted following removal of the protecting group blocking the amine.

Compounds containing branched bridging moieties, i.e., where A and/or B bears an alkyl substituent, may be produced using methods adapted from Sun, U.S. Pat. No. 5,206,249, the full contents of which are hereby incorporated herein by reference.

The bis-naphthalimide so obtained is used as is or it can be acidified with the appropriate mineral or organic acid to produce a pharmaceutically acceptable salt, e.g. the methanesulfonate or the acetate salt, which can be recovered by filtration. Salts of free base can also be prepared by acidifying a suspension of free base in ethyl alcohol, dichloromethane, ether, etc. with the appropriate mineral or organic acid and collecting the so formed solid by filtration. Other acids for salt formation are known in the art, see e.g., Brana et al., U.S. Pat. No. 4,874,883.

The 1,8-naphthalic anhydrides II and the corresponding polyamines of Formula III are commercially available or can be prepared by methods known in the literature. Branched polyamines may be synthesized and incorporated into bis-naphthalimides of this invention using desired anyhdride moieties by the methods of U.S. Pat. No. 5,206,249 (Sun).

This invention further encompasses pharmaceutical compositions containing a tumor-inhibiting compound of this invention together with a pharmaceutically acceptable carrier. This invention also relates to methods for treating a tumor in a mammal comprising administration of a tumor-inhibiting amount of a compound of this invention to a mammal bearing such a tumor. The compounds of this invention may be formulated into pharmaceutical compositions and administered to patients using conventional materials and methods such as are described in Brana et al, U.S. Pat. No. 4,874,883 and Sun, U.S. Pat. No. 5,206,249 (the contents of both of which are hereby incorporated herein by reference). See especially U.S. Pat. No. 5,206,249 at column 22, line 10 through the end of column 23.

Compounds of this invention have cytotoxic activity useful in the treatment of various cancers. These compounds can be evaluated for relative efficacy in in vitro and in vivo models such as are generally accepted in this art, including those described in Sun, U.S. Pat. No. 5,206,249 (see especially column 19 to column 22, line 9). Efficacy in such models is indicative of utility in the treatment of solid tumors in human patients and evidences important therapeutic utility in the treatment of cancer, particularly solid tumor carcinomas.

A. In vitro methodology

Cytotoxicity may be measured using a standard methodology for adherent cell lines such as the microculture tetrazolium assay (MTT). Details of 30 this assay have been published (Alley, MC et al, Cancer Research 48:589–601, 1988). Exponentially growing cultures of tumor cells such as the HT-29 colon carcinoma or LX-1 lung tumor are used to make microtiter plate cultures. Cells are seeded at 5000–20,000 cells per well in 96-well plates (in 150 μl of media), and grown overnight at 37° C. Test compounds are added, in 10-fold dilutions varying from $10^{-4}$M to $10^{-10}$M.

Cells are then incubated for 48–72 hours. To determine the number of viable cells in each well, the MTT dye is added (50 μl of 3 mg/ml solution of 3-(4,5-dimethylthiazol-2-yl)-2,5-diphenyltetrazolium bromide in saline). This mixture is incubated at 37° C. for 5 hours, and then 50 μl of 25% SDS, pH2 is added to each well. After an overnight incubation, the absorbance of each well at 550 nm is read using an ELISA reader. The values for the mean+/–SD of data from quadruplicate wells are calculated, using the formula %T/C (%viable cells treated/control).

$$\frac{OD \text{ of treated cells}}{OD \text{ of control cells}} \times 100 = \% \, T/C$$

The concentration of test compound which gives a T/C of 50% growth inhibition is designated as the $IC_{50}$ B. In Vivo Methodology Compounds of this invention may be further tested in any of the various preclinical assays for in vivo activity which are indicative of clinical utility. Such assays may be conducted with nude mice into which tumor tissue, preferably of human origin, has been transplanted ("xenografted"), as is well known in this field. Test compounds are evaluated for their antitumor efficacy following administration to the xenograft-bearing mice.

More specifically, human tumors which have been grown in athymic nude mice are transplanted into new recipient animals, using tumor fragments which are about 50 mg in size. The day of transplantation is designated as day 0. Six to ten days later, mice are treated with the test compounds given as an intravenous or intraperitoneal injection, in groups of 5–10 mice at each dose. Compounds are given daily for 5 days, 10 days or 15 days, at doses from 10–100 mg/kg body weight. Tumor diameters and body weights are measured twice weekly. Tumor volumes are calculated using the diameters measured with Vernier calipers, and the formula:

(length×width²)/2=mm³ (tumor volume)

Mean tumor volumes are calculated for each treatment group, and T/C values determined for each group relative to the untreated control tumors. The data may be evaluated as follows. A T/C value of 1.0 or greater indicates that the compound had no effect on tumor growth, while values<1.0 indicate some reduction in tumor mass. Values of 0.15–0.49 may be considered to reflect moderate activity, <0.01–0.14 good to excellent activity. Outstanding activity indicates a compound which gives complete regressions of tumor material (no visible tumor mass following therapy). Compounds yielding TIC values>0.50 are considered inactive.

The invention can be further understood by referring to the following examples wherein parts and percentages are by weight unless otherwise specified.

EXAMPLES

Example 1
N,N'-Bis[2-(l,8-naphthalimido)ethyl]-1,3-diaminopropane.

A mixture of 4 g (20 mmol) of 1,8-naphthalic anhydride and 1.6 g (10 mmol) of N,N'-Bis(2-aminoethyl)-1,3-diaminopropane was heated in dioxane (40 ml) at reflux temperature for five hours. The precipitated solid was filtered, washed, dried and recrystallized from toluene. 3 g (58%) of N,N'- Bis[2-(1,8-naphthalimido)ethyl]-1,3-diaminopropane were obtained. M.p.160° C. (Toluene). $^1$H-NMR (CF$_3$COOD) δ=2.54 (m,2H); 3.58(t, J=7.5, 4H); 3.86 (t, J=4.9, 4H); 4.83 (t, J=4.8, 4H); 7.93(t, J=7.4, 4H); 8.48(d, J=8.3, 4H); 8.73 (d, J=7.4, 4H). Anal. Calculated for $C_{31}H_{28}N_4O_4$; C 71.50; H 5.42; N 10.76. Found: C 71.20; H 5.48; N 10.59.Acetate m.p. 134° C. Methanesulfonate m.p. 215° C.

Example 2
N,N'-Bis[2-(4-Chloro-1,8-Naphthalimido)ethyl]-1,3-Diaminopropane

A mixture of 4 g (17 mmol) of 4-chloro-1,8-naphthalic anhydride and 1.3 g (8.5 mmol) of N,N'-bis(2-aminoethyl)-1,3-diaminopropane was heated in dioxane (40 ml) at reflux temperature for five hours. The precipited solid was filtered, washed, dried and recrystallized from toluene. 2.9 g (59%) of N,N'-bis[2-(4-chloro-1,8- naphthalimido)ethyl]-1,3-diaminopropane were obtained. M.p. 151° C (Toluene). $^1$H-NMR (CF$_3$COOD) δ=2.54 (s,2H); 3.57 (t, J=7.4, 4H); 3.86 (s,4H); 4.81 (s,4H); 8.00 (d, J=7.9, 2H); 8.04 (d, J=8.6; 2H); 8.62 (d, J=8.0; 2H); 8.78 (d, J=7.3 2E); 8.90 (d, J=8.2, 2H). Anal. calculated for $C_{31}H_{26}N_4O_4Cl_2$: C 63.16; H 4.44; N 9.50. Found: C 62.89; H 4.49; N 9.20.

Example 3
N,N'-Bis[2-(3-nitro-1,8-naphthalimido)ethyl]-1,3-diaminopropane.

As example 1. Yield 64%. M.p. 215° C. (DMF).

Example 4
N,N'-Bis[2-(4,5-dimethylene-1,8-naphthalimido)ethyl]-1,3-diaminopropane.

As example 1. Yield 51%. M.p. 209° C. (Toluene).

Example 5
N,N'-Bis[2-(2-hydroxyl-1,8-naphthalimido)ethyl]-1,3-diaminopropane.

As example 1. Yield 29%. M.p. 103° C. (EtOH).

Example 6
N,N'-Bis[2-(3-hydroxy-1,8-naphthalimido)ethyl]-1,3-diaminopropane.

As example 1. Yield 75%. M.p. 207° C. (DMF).

Example 7
N,N'-Bis[2-(4-hydroxy-1,8-naphthalimido)ethyl]-1,3-diaminopropane.

As example 1. Yield 38%. M.p. 196° C. (EtOH).

Example 8
N,N'-Bis[2-(4-bromo-1,8-naphthalimido)ethyl]-1,3-diaminoethane.

As example 1. Yield 58%. M.p. 182° C. (EtOH).

Example 9
N,N1-Bis[2-(2-methyl-1,8-naphthalimido)ethyl]-1,3-diaminopropane.

As example 1. Yield 45%. M.p. 220° C. (EtOH).

Example 10
N,N'-Bis[2-(3-amino-1,8-naphthalimido)ethyl]-1,3-diaminopropane.

As example 1. Yield 72%. M.p. 200° C. (DMF-H$_2$0).

Example 11
N,N'-Bis[2-(3-acetylamino-1,8-naphthalimido)ethyl]-1,3-diaminopropane.

As example 1. Yield 63%. M.p. 240° C. (DMF-H$_2$O).

Example 12
N,N'-Bis[2-(4-nitro-1,8-naphthalimido)ethyl]-1,3-diaminopropane.

As example 1. Yield 32%. M.p. 162° C. (Toluene).

Example 13
N,N'-Bis[2-(4,5-dimethyl-1,8-naphthalimido)ethyl]-1,3-diaminopropane.

As example 1. Yield 74%. M.p. 205° C. (Toluene).

Example 14
(R,R)-N,N'-Bis[2-(3-acetylamino-1,8-naphthalimido)propyl]-1,2 diaminoethane.

As example 1Yield 40%. M.p. 168° C. (Xylene).

Example 15
N,N'-Bis[2-(1,8-naphthalimido)ethyl]-N,N'-dimethyl-1,3-diaminopropane.

2 g (3.8 mmol) of N,N'-Bis[2-(1,8-naphthalimido)ethyl]-1,3-diaminopropane were dissolved in 10 ml of formic acid and 4 ml of formaldehyde were added to the solution. The reaction mixture was heated at reflux temperature for four hours, the formic acid was removed in vacuum to give a residue which was neutralized with sodium bicarbonate. The obtained solid was filtered and recrystallized from ethanol to give 1 g (47%) of N,N'-Bis-[2-(1,8-naphthalimido)ethyl]-N,N$^1$-dimethyl-1,3-diaminopropane.

M.p. 133° C. (Ethanol). $^1$H-NMR (CF$_3$__-COOD) δ=2.70 (m,2H); 3.32 (s,6H); 3.63(m,2H); 3.89 (m,6H); 4.85 (m,4H); 7.90 (m,4H); 8.43 (d, J=8.2 Hz, 2H); 8.47(d, J=8.2Hz, 2H); 8.71 (t, J=8 Hz, 4H). Anal. Calc. for $C_{33}H_{32}N_4O_4$: C, 72.24; H, 5.87; N, 10.21.Found: C, 72.07; H, 5.72; N, 10.25.

Example 16
N,N'-Bis-[2-(1,8-naphthalimido)ethyl]-N,N'-diethyl-1,3-diaminopropane.

2 g (3.8 mmol) N,N'-Bis-[2-(1,8-naphthalimido)ethyl]-1,3-diaminopropane were dissolved in 50ml of acetic acid and the solution was heated to 50°–55° C. for 10 h. The reaction was cooled and quenched with 25 ml of water and the solution was extracted with methylene chloride. The extracts were dried and the solvent was removed to vacuum. The residual oil was chromatographed in column yielding 1 g (45%) of N,N'-Bis-[2-(1,8-naphthalimido)- ethyl]-N,N'-diethyl-1,3-diaminopropane. M.p. 106° C. (EtOH). 1 H NMR (CF$_3$COOD) δ=1.54 (t, J=7.1 HZ, 6H); 2.70 (m, 2H); 3.75 (m, 8H); 3.86
4.82 (m, 4H); 7.86 (t, J=7.8Hz, 8H); 8.38 (d, J=2.9Hz, 2H); 8.42 (d, J=3.0 Hz, 2H); 8.66 (d, J=7.4 Hz, 4H).

Example 17
N,N'-Bis-[2-(1,8-naphthalimido)ethyl]-N,N$^1$-dibutyl-1,3-diaminopropane.

1 g (1.9 mmol) of N,N'-Bis-[2-(1,8-naphthalimido)ethyl]-1,3-diamino- propane, 0.2 g (3.8 mmol) of KOH and 15 mg of Tetrabutylammoniumbromide were mixed in a flask and put into ultrasonic bath for 15 minutes.

Then, 800 mg (5.8 mmol) of n-butylbromide were added to the mixture and the reaction was heated to 80° C. for 8 h. The product was extracted with CH$_2$Cl$_2$ concentrated and chromatographed in column yielding 0.48 g (40%) of N,N'-Bis[2-(1,8-naphthalimido)ethyl]-N,N'-dibutyl-1,3-diaminopropane. M.p. 245° C. (EtOH). $^1$H NMR (CF$_3$COOD) δ=1.08 (t, J=7.0 Hz, 6H); 1.57 (m, 4H); 1.95 (m, 4H); 2.87 (m, 2H); 3.60 (m, 4H); 3.92 (m, 8H); 4.88 (m, 4H); 7.90 (m, 4H); 8.47 (t, J=7.4 Hz, 4H); 8.74 (m, 4H).

Example 18
N,N'-Bis[2-(1,8-naphthalimido)ethyl]-1,4-diaminobutane.

The title compound is produced as described in Example 1, but using N,N'-Bis(2-aminoethyl)-1,4-diaminobutane in place of N,N-Bis(2-aminoethyl)- 1,3-diaminopropane. Yield 30% M.p. 186° (Toluene-n-Heptane).

Example 24
N,N'-Bis[2-(1,8-naphthalimido)-1-propyl]-1,2-diaminoethane.

As Example 1.Yield 53%. M.p. 158° C. (Toluene). Methanesulfonate m.p. 245° C. (MeOH).

What is claimed is:

1. The method of treating colon carcinoma or breast cancer in a mammal comprising
    administering to the mammal a tumor-inhibiting amount of a compound of formula (I)

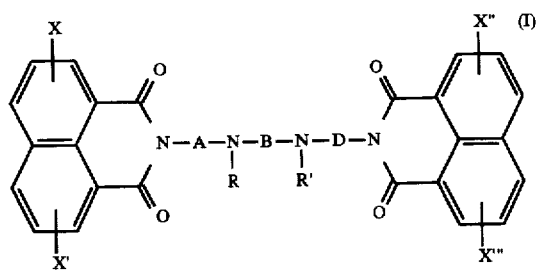

wherein X, X', X", and X'" are identical or different and are selected from the group consisting of H, NH$_2$, NHCOCH$_3$, C$_{1-6}$ alkylamino, di-C$_{1-6}$ alkylamino, OH, C$_{1-6}$ alkoxy, halogen, trihalomethyl, C$_{1-6}$ alkyl, formyl, C$_{1-6}$alkylcarbonyl, ureyl, and C$_{1-6}$ alkylureyl; R and R' are H, C$_{1-4}$ alkyl, aryl or benzyl; A and D are identical or different and are —CH$_2$—CH$_2$—, which may be optionally substituted with a C$_{1-4}$ alkyl substituent, and B is —(CH$_2$)$_n$—, wherein n is 3 or 4, and may be optionally substituted with a C$_{1-4}$—alkyl group.

2. The method of claim 1 wherein X, X', X" and X'" are identical or different and are selected from the group consisting of H, NH$_2$, NH-lower acyl and halogen.

3. The method of claim 1 wherein at least one of X, X', X" and X'" is NH$_2$ or NH-lower acyl.

4. The method of claim 1, wherein X, X', X"and X'" are H,—A—NR—B—NR'—D— is —CH$_2$—CH$_2$—NH—CH$_2$—CH$_2$—CH$_2$—CH$_2$—NH—CH$_2$—CH$_2$.

5. The method of claim 1, wherein X, X', X" and X'" are H, —A—NR—B—NR'—D— is —CH$_2$—CH$_2$—NH—CH$_2$—CH$_2$—CH$_2$—NH—CH$_2$—CH$_2$.

6. The method of claim 1, wherein X and X'" are NH$_2$, X'and X" are H and—A—NR—B—NR'—D— is —CH$_2$—CH$_2$—NH—CH$_2$—CH$_2$—CH$_2$—NH—CH$_2$—CH$_2$—.

7. The method of claim 1, wherein X and X'" are NHCOCH$_3$, X' and X" are H, and—A—NR—B—NR'—D— is —CH$_2$—CH$_2$—NH—CH$_2$—CH$_2$—CH$_2$—NH—CH$_2$—CH$_2$—.

* * * * *